(12) United States Patent
Yoshii et al.

(10) Patent No.: US 6,849,163 B2
(45) Date of Patent: Feb. 1, 2005

(54) METHOD FOR PRODUCING TETRAFLUOROETHYLENE

(75) Inventors: Shigeyuki Yoshii, Settsu (JP); Yukio Homoto, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 289 days.

(21) Appl. No.: 10/220,316

(22) PCT Filed: Feb. 27, 2001

(86) PCT No.: PCT/JP01/01444

§ 371 (c)(1),
(2), (4) Date: Oct. 7, 2002

(87) PCT Pub. No.: WO01/64612

PCT Pub. Date: Sep. 7, 2001

(65) Prior Publication Data

US 2003/0098228 A1 May 29, 2003

(30) Foreign Application Priority Data

Feb. 29, 2000 (JP) ......................... 2000-053610

(51) Int. Cl.[7] .............................. B01D 3/14; B01D 3/36; C07C 17/383; C07C 21/18
(52) U.S. Cl. ........................... 203/67; 203/74; 570/136; 570/153; 570/178
(58) Field of Search ............................. 203/67, 71, 73, 203/74; 570/136, 153, 178

(56) References Cited

U.S. PATENT DOCUMENTS

| | | | |
|---|---|---|---|
| 3,101,304 A | * | 8/1963 | Wiist ............................. 203/67 |
| 3,221,070 A | * | 11/1965 | Okamura et al. ........... 570/179 |
| 3,834,996 A | | 9/1974 | Also et al. |
| 4,898,645 A | * | 2/1990 | Voigt et al. ................. 203/67 |

FOREIGN PATENT DOCUMENTS

| | | | |
|---|---|---|---|
| EP | 0 038 970 | * | 4/1981 |
| EP | 307673 A1 | | 2/1990 |
| JP | 40-18283 | | 8/1940 |
| JP | 39-19624 B1 | | 9/1964 |
| JP | 4810444 B1 | | 4/1973 |
| JP | 7-233104 A | | 9/1995 |

* cited by examiner

Primary Examiner—Virginia Manoharan
(74) Attorney, Agent, or Firm—Birch, Stewart, Kolasch & Birch, LLP

(57) ABSTRACT

There is provided a process for recovering tetrafluoroethylene wherein an amount of energy required to obtain TFE is reduced.

In the process for producing a TFE mixture as an intended mixture which contains TFE at a higher concentration from a raw material mixture (10) which contains TFE, a component of which boiling point is lower than that of TFE and a component of which boiling point is higher than that of TFE, (1) the raw material is subjected to a preliminary distillation treatment (12) so as to obtain (a) a first fraction (15) which contains at least a portion of the component of which boiling point is higher than that of TFE and (b) a second fraction (14) as the balance which contains TFE and the component of which boiling point is lower than that of TFE, and then (2) the second fraction is subjected to a main distillation treatment (16) so as to obtain (c) a third faction (20) formed by distilling off the component of which boiling point is lower than that of TFE, and (d) a fourth fraction (18) as the intended mixture being the balance which contains TFE.

15 Claims, 3 Drawing Sheets

METHOD FOR PRODUCING TETRAFLUOROETHYLENE

This application is the national phase under 35 U.S.C. §371 of PCT International Application No. PCT/JP01/01444 which has an International filing date of Feb. 27, 2001, which designated the United States of America.

TECHNICAL FIELD

The present invention relates to a process for producing tetrafluoroethylene ($CF_2=CF_2$, which is hereinafter referred to also as "TFE"). Particularly, the present invention relates to a process for producing tetrafluoroethylene wherein a tetrafluoroethylene mixture is obtained from a raw material mixture which comprises tetrafluoroethylene, a component of which boiling point is higher than that of TFE (such as trifluoroethylene ($CF_2=CHF$), monochloro-difluoromethane ($CHClF_2$, which is hereinafter referred to also as "R22") and so on) and a component of which boiling point is lower than that of TFE (such as trifluoromethane ($CHF_3$, which is hereinafter referred to as also "R23") and so on), and a tetrafluoroethylene concentration of the tetrafluoroethylene mixture is increased relative to that of the raw material mixture.

Such process is applicable to a tetrafluoroethylene production process which is characterized in that a mixture comprising tetrafluoroethylene is recovered from a reaction mixture comprising, as a main component, tetrafluoroethylene which is formed through a high temperature pyrolysis, as a main component, of monochloro-difluoromethane, and a tetrafluoroethylene concentration of the mixture is higher than that of the reaction mixture.

BACKGROUND ART

The reaction mixture formed in the production process of tetrafluoroethylene by the high temperature pyrolysis of monochloro-difluoromethane as described above contains various by-products in addition to TFE as the intended product. As such by-products, trifluoroethylene, difluoromethane ($CH_2F_2$, which is hereinafter referred to also as "R32") and so on may be exemplified. Also, the reaction mixture usually contains R22 as an unreacted component.

As the process for recovering TFE from the reaction mixture, Japanese Patent Kokai Publication No. 7-233104 discloses a process which uses two distillation apparatuses. In the process, the first distillation apparatus separates the reaction product into a higher boiling point fraction which contains TFE and a lower boiling point fraction which boils at a lower temperature than TFE, and then the second distillation apparatus separates the higher boiling point fraction which contains TFE into TFE and a higher boiling point fraction which boils at a higher temperature than TFE.

The process using the distillation apparatuses as described above generally requires a reflux, and a reflux ratio thereof is large so that a large amount of energy (usually heating energy through steam) is required. Therefore, it is desirable to provide a process which reduces energy consumption so that TFE is effectively recovered.

DISCLOSURE OF INVENTION

It is, therefore, an object of the present invention to provide a new process for producing TFE by recovering TFE while reducing an amount of energy as a whole which is required for obtaining TFE.

In a first aspect, the present invention provides a process for producing tetrafluoroethylene wherein a tetrafluoroethylene mixture is obtained as an intended mixture from a raw material mixture which comprises tetrafluoroethylene, at least one component of which boiling point is lower than that of TFE (which is hereinafter referred to merely also as a "lower boiling component") and at least one component of which boiling point is higher than that of TFE (which is hereinafter referred to merely also as a "higher boiling component"), and a tetrafluoroethylene concentration of the tetrafluoroethylene mixture is larger than that of the raw material mixture, the process being characterized in that:

(1) subjecting said raw material mixture to a preliminary distillation treatment so as to obtain:
(a) a first fraction which comprises at least a portion of said higher boiling component, and
(b) a second fraction as the balance of the raw material mixture which fraction comprises tetrafluoroethylene and said lower boiling component, and
(2) then subjecting the second fraction to a main distillation treatment so as to obtain:
(c) a third faction formed by distilling off said lower boiling component, and
(d) a fourth fraction as the intended mixture being the balance of the second fraction which fraction comprises tetrafluoroethylene.

In a first embodiment of the first aspect according to the present invention, the first fraction comprises a portion of said higher boiling component which is contained in the raw material mixture. In this embodiment, the second fraction comprises also the balance of the higher boiling component, and therefore the fourth fraction contains such balance. However, the TFE concentration of the fourth fraction is larger than that of the raw material mixture. In order to obtain a fraction which contains TFE at a further higher concentration, the fourth fraction is subjected to a post-distillation treatment so that a fifth fraction which contains TFE at the further higher concentration as well as a sixth fraction as the balance thereof which contains the higher boiling component is obtained.

In a second embodiment of the first aspect according to the present invention, the first fraction comprises substantially all of said higher boiling component which is contained in the raw material mixture. In this embodiment, the fourth fraction contains substantially no higher boiling component, and therefore it contains TFE at a higher concentration.

It is noted that the higher boiling component and the lower boiling component are referred to on the basis of their boiling points, respectively. However, when the raw material mixture contains a component which forms an azeotrope having a minimum azeotropic boiling point with tetrafluoroethylene, the mixture is regarded to contain a single lower boiling component having said minimum azeotropic boiling point in amounts of tetrafluoroethylene and the former component which amounts correspond to a composition of the azeotrope even though the former component itself has a higher boiling point than that of tetrafluoroethylene.

For example, when the raw material mixture contains a large amount of tetrafluoroethylene, an azeotrope of tetrafluoroethylene and said former component is regarded to be a single lower boiling component and the rest of tetrafluoroethylene is regarded to be another component. That is, such raw material mixture contains two kinds of components (one is the azeotrope and the other is TFE of which amount does not form the azeotrope). For example, it has been already known that TFE and R32 form an azeotrope having a minimum boiling point, as to which reference can be made to Japanese Patent Kokoku Publication No. 40-18283.

It is noted that R22, hexafluoropropylene, perfluorocyclobutane and so on can be exemplified as the higher boiling components. Also, it is noted that trifluoromethane, 1,1-difluoroethylene, TFE/R32 azeotrope and so on can be exemplified as the lower boiling components.

In a second aspect of the present invention, the raw material mixture in the process of the first aspect comprises tetrafluoroethylene (TFE), difluoromethane (R32), and monochloro-difluoromethane (R22) with a proviso that an amount of TFE is larger than an amount which is necessary to form an azeotrope with R32 contained in the raw material mixture. Therefore, the raw material mixture contains TFE, the R32/TFE azeotrope as the lower boiling component and R22 as the higher boiling component.

Thus, in the second aspect, the process for producing tetrafluoroethylene according to the present invention is characterized in that:

(1) subjecting the raw material mixture to the preliminary distillation treatment so as to obtain:
 (a) the first fraction comprising, as a main component, monochloro-difluoromethane which fraction contains at least a portion of monochloro-difluoromethane contained in the raw material mixture, and
 (b) the second fraction as the balance of the raw material mixture, and
(2) then subjecting the second fraction to the main distillation treatment so as to obtain from the second fraction:
 (c) the third faction comprising, as a main component, an azeotrope of difluoromethane and tetrafluoroethylene, and
 (d) the fourth fraction as the balance of the second fraction which contains the balance of tetrafluoroethylene and which is the intended mixture.

It is noted that the second fraction contains monochloro-difluoromethane at a concentration which is lower than that of the raw material mixture. The fourth fraction contains, together as a main component (when the following two components are combined together), tetrafluoroethylene and monochloro-difluoromethane of which amount corresponds to difference between its amount in the raw material mixture and its amount of said at least a portion contained in the first fraction.

The raw material mixture may further contain trifluoroethylene. In such case, trifluoroethylene behaves inherently in the above process, that is, it may be contained by various fractions depending on conditions under which the above process is carried out.

In a first embodiment of the second aspect of the present invention,
(1) the preliminary distillation treatment provides the first fraction which contains, as a main component, a portion of R22 contained in the raw material mixture as well as the second fraction which is the balance of the raw material mixture, and then
(2) the distillation treatment of the second fraction as the main distillation treatment provides the third fraction which contains, as a main component, the azeotrope having a minimum boiling point of R32 and TFE as well as the fourth fraction as the intended mixture which is the balance of the second fraction. The fourth fraction contains, together as a main component (when the following two components are combined together), TFE and R22 which is contained in the second fraction of the preliminary distillation treatment.

Therefore, it is preferable that the fourth fraction is subjected to a post-distillation treatment thereafter to provide a fifth fraction which contains TFE as a main component and a sixth fraction which is the balance of the fifth fraction and which contains R22 as a main component, wherein the TFE concentration of the fifth fraction becomes further higher than that of the fourth fraction.

In the first embodiment of the second aspect as described above, for example, (1) using a distillation column which performs the preliminary distillation treatment, the first fraction which contains, as a main component, a portion of R22 contained in the raw material mixture is obtained from a stripping section and preferably from a bottom part (or a still) of the column, and the balance of the raw material mixture is obtained as the second fraction from a enriching section and preferably from a top part of the column, and (2) using a distillation column which performs the main distillation treatment of the second fraction, the third fraction which contains, as a main component, the azeotrope of R32 and TFE having a minimum boiling point is obtained, and the fourth fraction as the intended mixture which is the balance of the second fraction and which contains, as a main component, TFE and R22 is obtained from a bottom part of the column.

Thereafter, using a distillation column which further performs the post-distillation treatment of the fourth fraction, the fifth fraction which contains TFE as a main component is obtained from an enriching section and preferably a top part of the column, and the sixth fraction which contains R22 as a main component and which is the balance of the fourth fraction is obtained from a stripping section and preferably a bottom part of the column.

In the preliminary distillation treatment, as to R22 contained in the raw material mixture, a portion of R22 is removed and the rest of R22 is contained in the second fraction. Thereafter, in the main distillation treatment, substantially all of R22 is contained in the fourth fraction. When the raw material mixture contains trifluoroethylene, it behaves together with R22, and therefore a portion of trifluoroethylene is contained in the first fraction, the rest thereof is contained in the second fraction, which is in turn contained in the fourth fraction, and finally contained in the sixth fraction.

As to R32, it is contained in the second fraction, and it is preferable that substantially all of R32 is contained in the third fraction through the main distillation treatment. However, a small amount of R32 may be contained in the fourth fraction, and in such case, it is present in the fifth fraction through the post-distillation treatment. An extent to which R32 may be present in the fourth fraction depends on an application of the fourth fraction to be obtained. Usually, R32 may be contained in the fourth fraction in a concentration of not larger than about 100 ppm by mol.

In a second embodiment of the second aspect as described above, for example, (1) through the preliminary distillation treatment, the first fraction which contains, as a main component, substantially all of R22 is obtained, and the balance thereof is obtained as the second fraction, and (2) then, through the main distillation treatment of the second fraction, the third fraction which contains, as a main component, the azeotrope of R32 and TFE having a minimum boiling point is obtained, and the fourth fraction as the intended mixture which is the balance of the second fraction and which contains TFE as a main component is obtained.

In this second embodiment, the removal of R22 into the first fraction through the preliminary distillation treatment in the first embodiment is carried out such that the first fraction contains not a portion of R22 but substantially all of R22, so that the fourth fraction does not substantially contain R22. Therefore, there is an advantage in that the intended mixture which contains TFE at a high concentration can be obtained even though the post-distillation treatment of the first embodiment is omitted.

In the process of the second embodiment of the second aspect as described above, for example (1) with a distillation column which performs the preliminary distillation treatment, the first fraction which contains, as a main component, substantially all of R22 is obtained from a stripping section and preferably a bottom part (or a still) of the column, and the balance of the raw material mixture is obtained as the second fraction from an enriching section and preferably a top part of the column, and (2) with a distillation column which performs the main distillation treatment of the second fraction, the third fraction which contains, as a main component, the azeotrope of R32 and TFE having a minimum boiling point is obtained from an enriching section and preferably a top part of the column, and the fourth fraction which is the balance of the second fraction and which contains TFE as a main component is obtained from a stripping section and preferably a bottom part of the column.

When the raw material mixture contains trifluoroethylene, it basically behaves together with R22. However, since the boiling point of trifluoroethylene is lower than that of R22, substantially all of trifluoroethylene does not necessarily behave together with R22. Depending on conditions, most of trifluoroethylene may be contained in the first fraction, and a small amount of trifluoroethylene as the balance thereof may be contained by the second fraction. In this case, such trifluoroethylene as the balance would be thereafter contained in the fourth fraction.

Also, R32 is contained in the second fraction, and it is preferably that substantially all of R32 is contained in the third fraction. However, a small amount of R32 may be present in the fourth fraction. Extents to which trifluoroethylene and R32 may be present in the fourth fraction depend on an application of the fourth fraction to be obtained. Usually, each of R32 and trifluoroethylene may be contained in the fourth fraction in a concentration of not larger than about 100 ppm by mol.

In any of the embodiments, it is often that R32 and trifluoroethylene are contained in the raw material mixture in small amounts. Since boiling points of them are between boiling points of TFE and R22, substantially complete separation of R32 and trifluoroethylene from TFE or R22 is not easy. Provided that no adverse effect is caused in the application of the TFE mixture as the intended mixture, no problem is caused even when insufficient separation results in contamination of the TFE mixture due to R32 and trifluoroethylene.

In any of the embodiments, the "enriching section" and "stripping section" intend to mean an upper part and a lower part respectively with respect to a raw material feeding plate of the distillation apparatus. The "top part" and the "bottom part" correspond to a "top or vicinity thereof" and a "bottom or vicinity thereof" of the distillation apparatus (such as a distillation column) respectively. The "vicinity" means that it is not necessarily the top or the bottom of the apparatus, and it may be not such a location but a location within for example ten theoretical plates from the top or the bottom of the column, and therefore for example side cut may be carried out. Concretely, withdrawal from the column may be carried out at a location of for example the twentieth actual plate from the top or the bottom instead of the withdrawal from the top or the bottom of the column.

The expression "most of TFE (or other compound if applicable)" herein means at least 80% of TFE (or other compound if applicable), preferably at least 95% of TFE (or other compound if applicable) and particularly preferably at least 99% of TFE (or other compound if applicable) which is contained in a mixture subjected to a corresponding distillation treatment (namely, a mixture supplied to such a treatment step), and also means that such an amount of TFE (or other compound if applicable) is contained in a corresponding fraction or mixture.

In addition, the expression "at least a portion of R22 (or a higher boiling component)" or "a portion of R22 (or a higher boiling component)" means a ratio which is greater than and may be a whole (or 100%). Such ratio is determined on the basis of energy-related conditions which are required to obtain the fourth fraction which is the intended mixture. When the "at least a portion of R22 (or a higher boiling component)" used in the preliminary distillation treatment means a ratio which is greater than zero and smaller than 100%, such ratio may be for example usually not smaller than 50%, preferably not smaller than 80% and more preferably not smaller than 95%. The ratio is based on an amount of R22 (or a higher boiling component) contained in a feed which is supplied to the preliminary distillation treatment.

It is noted that mere reference to "a portion of R32 (or trifluoroethylene or HB (which will be described below))" means a relatively small ratio of R32 (or trifluoroethylene or HB). Such ratio may be for example usually not greater than 30%, preferably not greater than 10% and more preferably not greater than 1%, and it may be a further smaller ratio as the case may be. When reference is made to "a main component" when two components being combined together, the sum of the both components is of a specific percentage value ratio as described above. That ratio is based on an amount of R32 (or trifluoroethylene or HB) contained in a feed contained in a corresponding distillation treatment.

In addition, the expression "main component" means that a large amount of a corresponding component is present. It may mean that the component is contained usually in an amount of at least 50% by mol, preferably at least 80% and more preferably at least 95% by mol.

Further, the expression "substantially all of R22 (or other corresponding compound)" does not mean exactly 100%, and it is not necessarily all provided that the intended tetrafluoroethylene mixture obtained according to the present invention is applicable to an intended application (optionally after a further purification treatment). In the above embodiments, it may mean usually 90–100%, preferably 95–100% and more preferably 99–100%.

In the process according to the second aspect of the present invention, the raw material mixture may contain, in addition to or in place of R22 as described above, a component of which boiling point is higher than that of TFE. As such higher boiling component, for example hexafluoropropylene, perfluorocyclobutane and so on may be exemplified. These higher boiling components may be considered to behave substantially similarly to R22.

The raw material mixture in the present invention is not particularly limited as far as it contains the above described components. The present invention is effective particularly when it contains R22 or the high boiling component(s) in a large amount. For example, the raw material mixture may contain R22 or the higher boiling component(s) in an amount of at least 25% by weight, preferably at least 40% by weight and more preferably 75% by weight. Concretely, the raw material mixture may be a reaction mixture obtained upon the production of tetrafluoroethylene by the pyrolysis of monochloro-difluoromethane, or a mixture obtained by pretreating such a reaction mixture (such as a mixture obtained by removing a compound(s) having a greatly lower boiling point and/or a compound having a greatly higher boiling point by a partial condensation treatment, an evaporation treatment or the like).

The raw material mixture contains for example 20–69% by weight of tetrafluoroethylene (TFE), 100–1000 ppm by weight of trifluoroethylene, 100–1000 ppm by weight of difluoromethane (R32) and 25–75% by weight of monochloro-difluoromethane, and further a lower boiling component(s) (of which boiling point is lower than that of TFE) of totally for example 0.5–5% by weight and/or a higher boiling component(s) (of which boiling point is higher than that of R22) of totally for example 5–30% by weight.

The preliminary distillation treatment, the main distillation treatment and the post-distillation treatment may be carried out under any suitable operation condition(s). Usually, the boiling point of each component of the raw material is low, the treatments are preferably carried out under pressure, and preferably continuously. For those treatments, the conventional apparatuses may be used.

According to the process of the present invention, since the component(s) of which boiling point is higher than that of TFE (such as R22, hexafluoropropylene, perfluorocyclobutane and so on) is removed beforehand from the raw material, and then the main distillation treatment is carried out so as to remove the lower boiling components(s), the reflux ratio which is required for the distillation treatment can be reduced, so that an amount of energy required for the separation can be reduced.

Figure 1:
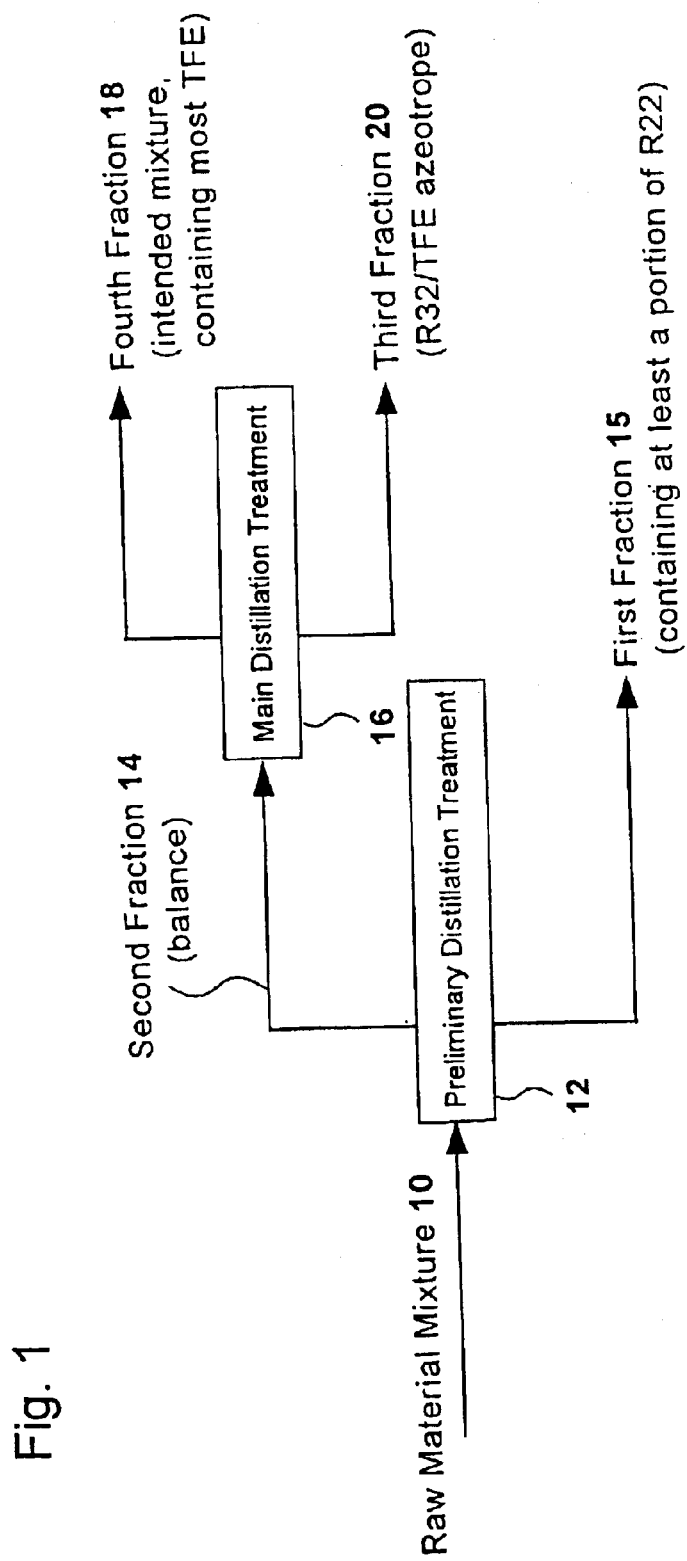
FIG. 1 is a flow sheet which schematically shows the process according to the present invention.

It is noted the numerals in the drawings denote the following:
10 . . . raw material mixture,
12 . . . preliminary distillation treatment,
14 . . . second fraction, 15 . . . first fraction,
16 . . . main distillation treatment,
18 . . . fourth fraction (intended mixture),
20 . . . third fraction,
22 . . . preliminary distillation treatment step,
24 . . . first fraction, 26 . . . second fraction,
28 . . . main distillation treatment step,
30 . . . fourth fraction, 32 . . . third fraction,
34 . . . post-distillation treatment step,
36 . . . fifth fraction, 38 . . . sixth fraction,
40 . . . preliminary distillation treatment step,
42 . . . first fraction, 44 . . . second fraction,
46 . . . main distillation treatment step,
48 . . . fourth fraction, 50 . . . third fraction.

CONCRETE EMBODIMENTS FOR CARRYING OUT THE INVENTION

The process according to the present invention, particularly the process of the second aspect will be further explained hereinafter in detail with reference to the accompanying drawings.

FIG. 1 schematically shows a flow sheet of the process according to the present invention. In the production process of TFE of the present invention, for example the raw material mixture 10 to be used contains TFE, trifluoroethylene, R32 and R22, and therefore it contains in addition to TFE, TFE/R32 azeotrope as the lower boiling component as well as trifluoroethylene and R22 as the higher boiling components. The raw material mixture may further contain 1,1-difluoroethylene, R23 and so on each having a further lower boiling point (which are referred to as "LB" generically). When the LB is contained, the LB behaves substantially together with the azeotrope of TFE and R32 having the minimum boiling point. In addition, the raw material mixture may further contain various components each having a boiling point higher than that of R22 (which are referred to as "HB" generically).

Such raw material mixture 10 is subjected to the preliminary distillation treatment step 12 to remove, from the raw material mixture 10, at least a portion of R22 beforehand which is contained in the first fraction 15, and the rest thereof is obtained as the second fraction 14. As to TFE and the LB if any in the raw material mixture, substantially all of them are contained in the second fraction 14. Depending on a separation performance of the preliminary distillation treatment step 12, a portion of trifluoroethylene and a portion of R32 may be contained in the first fraction 15, and the rest thereof (most of trifluoroethylene and R32) is contained in the second fraction 14. Also, when the HB is contained in the raw material 10, the HB behaves substantially together with said at least a portion of R22, that is, substantially all of the HB is contained in the first fraction. However, depending on the separation performance of the preliminary distillation treatment step 12, a portion of the HB may be contained in the second fraction 14.

The second fraction 14 is subjected to the main distillation treatment step 16, so that it is separated into the third fraction 20 which contains R32, and preferably substantially all of R32 as the azeotrope with TFE as well as the fourth fraction 18 as the intended mixture which contains most of TFE. Substantially all of R22 and trifluoroethylene contained in the second fraction 14 is contained in the fourth fraction. Depending on the separation performance of the main distillation treatment step 16, a portion of R32 may be contained in the forth fraction. When the LB is contained in the raw material mixture, the LB is contained in the second fraction, and substantially all of the LB is finally contained in the third fraction.

In this embodiment, the fourth fraction 18 can be obtained as the tetrafluoroethylene mixture which contains tetrafluoroethylene at a concentration which is higher than that of the raw material mixture. In this case, even though a reflux ration of the main distillation treatment 16 is reduced, R32 can be readily separated as an azeotrope with TFE from the remaining of TFE. In the process explained with reference to FIG. 1 as described above, in addition to or in place of R22, the raw material mixture may contain hexafluoropropylene and/or perfluorocyclobutane, wherein hexafluoropropylene and/or perfluorocyclobutane behave as described above in place of R22 or behave together with R22.

Figure 2:
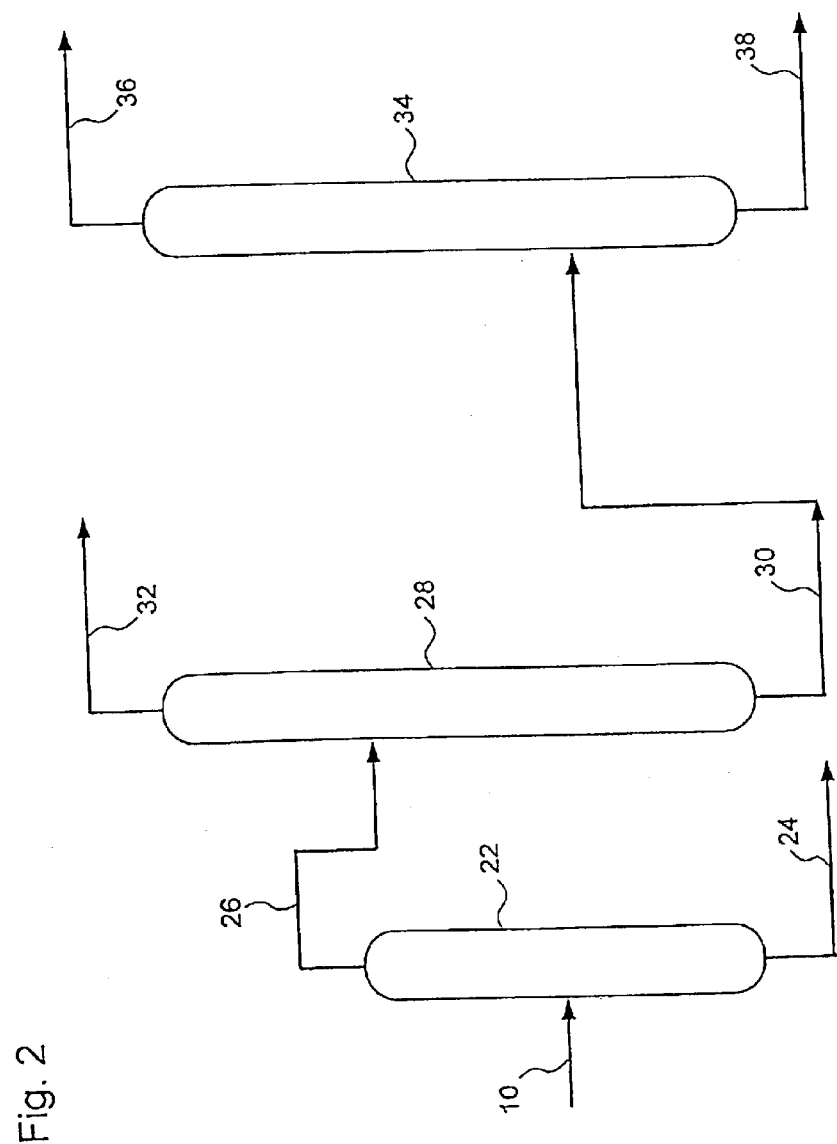
FIG. 2 is a flow sheet which schematically shows the first embodiment of the second aspect of the process according to the present invention.

FIG. 2 schematically shows the process of the present invention according to the first embodiment of the second aspect.

The raw material mixture 10 which is the same as described above is supplied to the preliminary distillation apparatus which performs the preliminary distillation treatment step 22 for the purpose of the preliminary distillation treatment which is performed beforehand and which removes from the raw material mixture 10, at least a portion (for example 90%) of R22 contained therein. From the bottom part of the preliminary distillation apparatus 22, the first fraction 24 which contains such portion of R22 is obtained and the balance of the raw material mixture is obtained from the top part as the second fraction 26.

Then, the second fraction 26 is supplied to the main distillation treatment step 28 so that the third fraction 32 is obtained which contains R32 as the minimum boiling azeotrope with TFE is obtained from the top part and the fourth fraction 30 as the intended mixture is obtained from the bottom part which fraction is the balance of the second fraction and which contains most of TFE. The above embodiment described with reference to FIG. 1 is substantially the same as this embodiment up to this stage.

As described above, the fourth fraction 30 which is obtained as the intended mixture contains, in addition to TFE, trifluoroethylene and R22 and as the case may be, R32. Therefore, in order to obtain a finally intended TFE having a higher purity, it is desirable to remove R22. Then, the fourth fraction 30 is supplied to the post-distillation treatment 34 so that the fourth fraction is separated into the fifth fraction 36 which contains substantially all of TFE and the sixth fraction 38 which substantially all of R22.

In this case, when the fourth fraction contains a small amount of R32, it forms the azeotrope with TFE and the azeotrope and the remaining of TFE are contained in the fifth fraction which is distilled off at the lower boiling component side. When the fourth fraction contains a small amount of trifluoroethylene, it is preferable that substantially all of trifluoroethylene is contained in the sixth fraction 38 together with R22. However, a portion of trifluoroethylene may be contained in the fifth fraction 36 depending on the performance of the post-distillation treatment.

It is preferable that the post-distillation treatment is so carried out that a purity of TFE of the fifth fraction is equal to or more than for example 99.9% by mol. The sixth fraction 38 contains substantially all of R22 which is contained in the second fraction 26. Such sixth fraction 38 and the first fraction 24 as they are or R22 separated therefrom (when necessary) may be recycled to and re-used in the reaction step for the production of TFE (i.e. the pyrolytic reaction step of R22).

Figure 3:
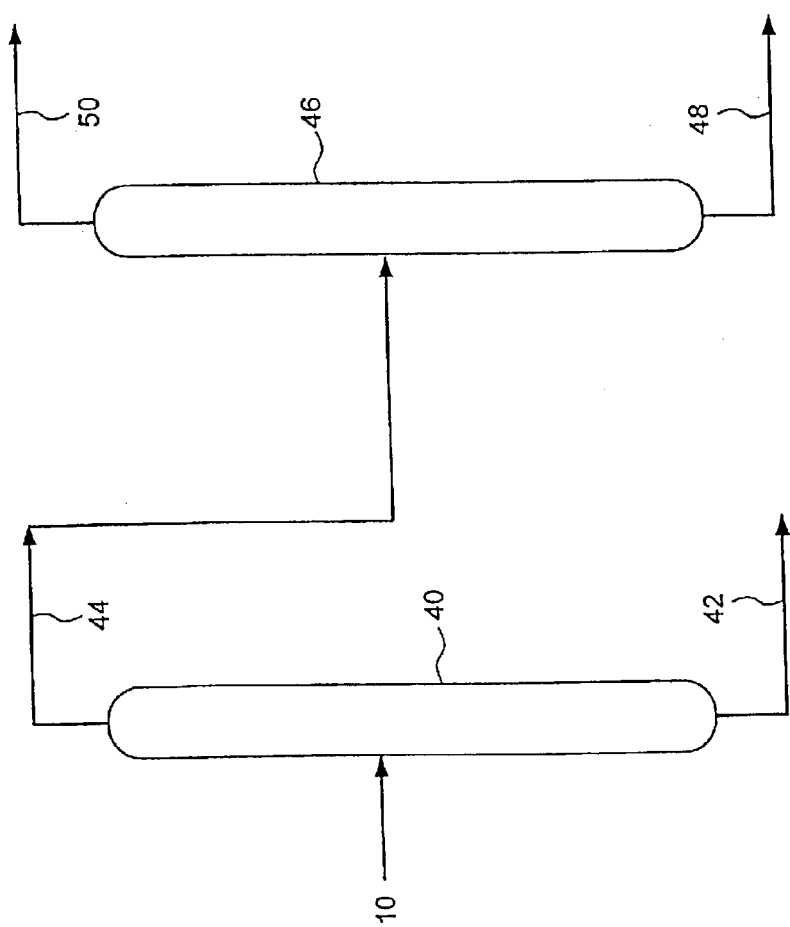
FIG. 3 is a flow sheet which schematically shows the second embodiment of the second aspect of the process according to the present invention.

FIG. 3 schematically shows the process of the present invention according to the second embodiment of the second aspect. In the shown embodiment, the preliminary distillation treatment is carried out as in the embodiment shown in FIG. 2. However, the shown embodiment is different from the embodiment shown in FIG. 2 in that substantially all of R22 contained in the raw material mixture is removed beforehand from the raw material mixture in the preliminary distillation treatment.

In the second embodiment shown in FIG. 3, the raw material mixture 10 which is the same as described above is supplied to the preliminary distillation treatment step 40 so that the first fraction 42 is obtained from the bottom part (or still) which contains substantially all of R22 contained in the raw material mixture and the second fraction 44 is obtained from the top part as the balance. The preliminary distillation treatment step is preferably carried out such that substantially all of TFE and a component of which boiling point is lower than TFE (including the azeotrope of R32 with TFE) such as LB is contained in the second fraction 44. As to trifluoroethylene contained in the raw material mixture, it is preferable that most of such trifluoroethylene is contained in the first fraction 42. When the raw material mixture contains HB, substantially all of the HB is contained in the first fraction 42. The first fraction 42 as it is or R22 separated therefrom when necessary may be recycled to and re-used in the reaction step for the production of TFE (i.e. the pyrolytic reaction step of R22).

Next, the second fraction 44 is supplied to the main distillation apparatus 46 which performs the main distillation treatment where the third fraction 50 is obtained from the top part which contains substantially all of R32 as the azeotrope with TFE as well as substantially all of the LB and the fourth fraction 48 is obtained as the intended mixture from the bottom part which contains most of TFE. When the second fraction 44 contains trifluoroethylene, it does not cause a problem since an amount of trifluoroethylene is small.

As clearly seen from the comparison of FIG. 2 with FIG. 3, there is an advantage in the second embodiment in that, as to the removal of R22 in the first embodiment, not a portion of but the substantially all of R22 is removed in the second embodiment so that the TFE mixture as the intended mixture which contains substantially no R22 can be obtained even without carrying out the post-distillation treatment.

EXAMPLES

Example 1

The preliminary distillation treatment was carried out by continuously supplying a raw material mixture of which composition is shown below at a rate of 1432 g/hr to a first column (having sixty theoretical plates and an inner diameter of 25 mm) which was operated at a pressure of 1.8 MPa-abs. (absolute pressure at column top, pressures referred to below are all the absolute pressures at the column top) and a reflux ratio at the column top of 14:

| | |
|---|---|
| trifluoromethane | 0.53 g/hr |
| tetrafluoroethylene | 642.97 g/hr |
| difluoromethane | 0.42 g/hr |
| trifluoroethylene | 0.23 g/hr |
| difluoro-monochloromethane and higher boiling components (hexafluoropropylene, tetrafluoromonochloroethane, perfluorocyclobutane and hexafluoromonochloropropane) totally | 787.75 g/hr |

A distillate of 646 g/hr was obtained from the top of the column and it had the following composition:

| | |
|---|---|
| trifluoromethane | 0.53 g/hr |
| tetrafluoroethylene | 641.58 g/hr |
| difluoromethane | 0.41 g/hr |
| trifluoroethylene | <0.0001 g/hr |

Then, the distillate obtained from the top of the first column was supplied to a second column (having sixty theoretical plates and an inner diameter of 25 mm) which was operated at a pressure of 1.6 MPa and a reflux ratio at the top of 77 so as to carry out the main distillation treatment and thereby a distillate of 29 g/hr was obtained from the top and it had the following composition:

| | |
|---|---|
| trifluoromethane | 0.53 g/hr |
| tetrafluoroethylene | 28.06 g/hr |
| difluoromethane | 0.41 g/hr |

A gas of 613.5 g/hr was withdrawn from a position of the fifty-fifth theoretical plate (provided that the top of the column is the first plate) by side-cutting and it had the following composition:

| | |
|---|---|
| tetrafluoroethylene | 613.5 g/hr |
| difluoromethane | <0.0001 g/hr |
| trifluoroethylene | <0.0001 g/hr |

Example 2

The preliminary distillation treatment was carried out by continuously supplying a raw material mixture of which composition is shown below at a rate of 1421 g/hr to a first column (having twenty theoretical plates and an inner diameter of 25 mm) which was operated at a pressure of 1.85 MPa (absolute top pressure) and a reflux ratio at the top of 3.8:

| | |
|---|---|
| trifluoromethane | 0.53 g/hr |
| tetrafluoroethylene | 632.40 g/hr |
| difluoromethane | 0.40 g/hr |
| trifluoroethylene | 0.25 g/hr |
| difluoro-monochloromethane and higher boiling components (hexafluoropropylene, tetrafluoro-monochloroethane, perfluorocyclobutane and hexafluoro-monochloropropane) totally | 787.42 g/hr |

A distillate of 719 g/hr was obtained from the top of the first column and it had the following composition:

| | |
|---|---|
| trifluoromethane | 0.53 g/hr |
| tetrafluoroethylene | 631.55 g/hr |
| difluoromethane | 0.25 g/hr |
| trifluoroethylene | 0.13 g/hr |
| difluoro-monochloromethane and higher boiling components (hexafluoropropylene, tetrafluoro-monochloroethane, perfluorocyclobutane and hexafluoro-monochloropropane) totally | 86.71 g/hr |

Then, the distillate obtained from the top of the first column was supplied to a second column (having sixty theoretical plates and an inner diameter of 25 mm) which was operated at a pressure of 1.8 MPa and a reflux ratio at the top of 143 so as to carry out the main distillation treatment and thereby a distillate of 18.8 g/hr was obtained from the top of the column and it had the following composition:

| | |
|---|---|
| trifluoromethane | 0.53 g/hr |
| tetrafluoroethylene | 18.02 g/hr |
| difluoromethane | 0.25 g/hr |

A bottom product of 700 g/hr was withdrawn from the still of the second column and supplied to a third column having sixty theoretical plates and an inner diameter of 25 mm) which was operated at a pressure of 1.6 MPa and a reflux ratio at the top of 17 so as to carry out the post-distillation treatment and thereby a distillate of 612.8 g/hr was obtained from the top of the column and it had the following composition:

| | |
|---|---|
| tetrafluoroethylene | 612.8 g/hr |
| difluoromethane | <0.0001 g/hr |
| trifluoroethylene | <0.0001 g/hr |

Comparative Example 1

As a comparative example, a process which is the same as that described in Japanese Patent Kokai Publication No. 7-233104 was carried out.

The distillation treatment was carried out by continuously supplying a raw material mixture of which composition is shown below at a rate of 1426 g/hr to a first column (having sixty theoretical plates and an inner diameter of 25 mm) which was operated at a pressure of 1.8 MPa and a reflux ratio at the top of 450:

| | |
|---|---|
| trifluoromethane | 0.58 g/hr |
| tetrafluoroethylene | 636.07 g/hr |
| difluoromethane | 0.43 g/hr |
| trifluoroethylene | 0.23 g/hr |
| difluoro-monochloromethane and higher boiling components (hexafluoropropylene, tetrafluoro-monochloroethane, perfluorocyclobutane and hexafluoro-monochloropropane) totally | 788.69 g/hr |

A distillate of totally 18.6 g/hr was obtained from the top of the first column and it had the following composition:

| | |
|---|---|
| trifluoromethane | 0.58 g/hr |
| tetrafluoroethylene | 17.59 g/hr |
| difluoromethane | 0.43 g/hr |

A bottom product from the first column of 1407 g/hr was supplied to a second column (having sixty theoretical plates and an inner diameter of 25 mm) which was operated at a pressure of 1.6 MPa and a reflux ratio at the top of 14 so as to carry out the distillation treatment of the bottom product, and thereby a distillate of 617.1 g/hr was obtained from the top of the column and it had the following composition:

| | |
|---|---|
| tetrafluoroethylene | 617.1 g/hr |
| difluoromethane | <0.0001 g/hr |
| trifluoroethylene | <0.0001 g/hr |

What is claimed is:

1. A process for producing tetrafluoroethylene wherein a tetrafluoroethylene mixture is obtained as an intended mixture from a raw material mixture which comprises tetrafluoroethylene, at least one component of which boiling point is lower than that of tetrafluoroethylene and at least one component of which boiling point is higher than that of tetrafluoroethylene, and a tetrafluoroethylene concentration of the tetrafluoroethylene intended mixture is larger than that of the raw material mixture, the process comprising:

(1) subjecting said raw material mixture to a preliminary distillation treatment so as to obtain:
  (a) a first fraction which comprises at least a portion of said higher boiling component, and
  (b) a second fraction as the balance of the raw material mixture which fraction comprises tetrafluoroethylene and said lower boiling component, and
(2) then subjecting the second fraction to a main distillation treatment so as to obtain:
  (c) a third faction formed by distilling off said lower boiling component, and
  (d) a fourth fraction as the intended mixture being the balance of the second fraction which fraction comprises tetrafluoroethylene.

2. The process according to claim 1 wherein the first fraction comprises a portion of said higher boiling component which is contained in the raw material mixture.

3. The process according to claim 2 wherein the fourth fraction is subjected to a post-distillation treatment so that a fifth fraction which contains tetrafluoroethylene at a higher concentration as well as a sixth fraction as the balance of the fourth fraction which six fraction contains the higher boiling component is obtained.

4. The process according to claim 2 or 3 wherein the portion of the higher boiling component is at least 80% of the higher boiling component which is contained in the raw material mixture.

5. The process according to claim 1 wherein the first fraction comprises substantially all of said higher boiling component which is contained in the raw material mixture.

6. The process according to claim 1 wherein the higher boiling component is contained at a concentration of at least 40% by weight in the raw material mixture.

7. The process according to claim 1 wherein the raw material mixture is a reaction mixture which is formed by a reaction in which tetrafluoroethylene is formed by pyrolysis of monochloro-difluoromethane.

8. A process for producing tetrafluoroethylene wherein a tetrafluoroethylene mixture is obtained as an intended mixture from a raw material mixture which comprises tetrafluoroethylene, difluoromethane and monochloro-difluoromethane, and a tetrafluoroethylene concentration of the tetrafluoroethylene intended mixture is larger than that of the raw material mixture, the process comprising:
(1) subjecting the raw material mixture to a preliminary distillation treatment so as to obtain:
  (a) a first fraction comprising, as a main component, monochloro-difluoromethane which fraction contains at least a portion of monochloro-difluoromethane contained in the raw material mixture, and
  (b) a second fraction as the balance of the raw material mixture, and
(2) then subjecting the second fraction to a main distillation treatment so as to obtain from the second fraction:
  (c) a third faction comprising, as a main component, an azeotrope of difluoromethane and tetrafluoroethylene, and
  (d) a fourth fraction as the balance of the second fraction which contains the balance of tetrafluoroethylene and which is the intended mixture.

9. The process according to claim 8 wherein
(1) the preliminary distillation treatment provides the first fraction which contains, as a main component, a portion of monochloro-difluoromethane contained in the raw material mixture as well as the second fraction which is the balance of the raw material mixture, and then
(2) the distillation treatment of the second fraction as the main distillation treatment provides the third fraction which contains, as a main component, the azeotrope having a minimum boiling point of difluoromethane and tetrafluoroethylene as well as the fourth fraction as the intended mixture which is the balance of the second fraction, and the fourth fraction contains, as a main component, tetrafluoroethylene and monochloro-difluoromethane which is contained in the second fraction of the preliminary distillation treatment.

10. The process according to claim 9 wherein the fourth fraction is further subjected to a post-distillation treatment so that a fifth fraction which contains tetrafluoroethylene as a main component and a sixth fraction which contains monochloro-difluoromethane as a main component and which is the balance of the fourth fraction are obtained.

11. The process according to claim 8 wherein
(1) through the preliminary distillation treatment, the first fraction is obtained which contains, as a main component, substantially all of monochloro-difluoromethane, and the balance thereof is obtained as the second fraction, and
(2) then, through the main distillation treatment of the second fraction, the third fraction is obtained which contains, as a main component, the azeotrope of difluoromethane and tetrafluoroethylene having a minimum boiling point, and the fourth fraction is obtained as the intended mixture which is the balance of the second fraction and which contains tetrafluoroethylene as a main component.

12. The process according to any one of claims 8 to 11 wherein the raw material mixture further comprises trifluoroethylene.

13. The process according to claim 8 wherein the monochloro-difluoromethane is contained at a concentration of at least 40% by weight in the raw material mixture.

14. The process according to claim 8 wherein the raw material mixture contains, in addition to monochloro-difluoromethane, a higher boiling component including hexafluoropropylene and/or perfluorocyclobutane.

15. The process according to any one of claim 8 wherein the raw material mixture is a reaction mixture which is formed by a reaction in which tetrafluoroethylene is formed by pyrolysis of monochloro-difluoromethane.

* * * * *